United States Patent
Friese et al.

[11] Patent Number: 5,998,012
[45] Date of Patent: Dec. 7, 1999

[54] CERAMIC LAYER SYSTEMS, PARTICULARLY FOR GAS SENSORS

[75] Inventors: Karl-Hermann Friese, Leonberg; Lothar Weber, Stuttgart; Werner Gruenwald, Gerlingen; Gert Lindemann, Lichtensteijn; Harald Neumann, Vaihingen; Ulrich Eisele, Stuttgart, all of Germany

[73] Assignee: Robert Bosch GmbH, Stuttgart, Germany

[21] Appl. No.: 08/716,376

[22] PCT Filed: Jan. 31, 1996

[86] PCT No.: PCT/DE96/00131

§ 371 Date: Sep. 19, 1996

§ 102(e) Date: Sep. 19, 1996

[87] PCT Pub. No.: WO96/24051

PCT Pub. Date: Aug. 8, 1996

[30] Foreign Application Priority Data

Feb. 2, 1995 [DE] Germany ............. 195 03 309

[51] Int. Cl.$^6$ .................................. B23B 17/00
[52] U.S. Cl. ............... 428/325; 428/328; 428/329; 428/701; 428/702; 264/669; 264/681
[58] Field of Search ................ 428/325, 206, 428/210, 328, 329, 701, 702; 264/669, 681

[56] References Cited

U.S. PATENT DOCUMENTS

| | | | |
|---|---|---|---|
| 4,221,650 | 9/1980 | Friese | 204/195 S |
| 4,283,441 | 8/1981 | Haecker | 427/126.2 |
| 4,296,148 | 10/1981 | Friese | 427/125 |
| 4,339,320 | 7/1982 | Friese | 204/195 S |
| 4,347,113 | 8/1982 | Fischer | 204/195 S |
| 5,310,575 | 5/1994 | Friese | 427/126.3 |
| 5,476,003 | 12/1995 | Neumann | 73/31.06 |
| 5,628,848 | 5/1997 | Friese | 156/89 |
| 5,681,784 | 10/1997 | Friese | 501/103 |
| 5,698,267 | 12/1997 | Friese | 427/430.1 |
| 5,709,786 | 1/1998 | Friese | 204/421 |

*Primary Examiner*—Timothy Speer
*Attorney, Agent, or Firm*—Venable; George H. Spencer; Ashley J. Wells

[57] ABSTRACT

A ceramic layer system including at least two layers having respective ion conductivities which are substantially different includes a substrate layer composed of a ceramic material and having substantially no ion conductivity; and at least one conducting layer positioned adjacent to the substrate layer, containing coated ceramic particles composed of ceramic particles composed of a ceramic material having no substantial ion conductivity which are coated with a material having a substantial ion conductivity so that each conducting layer of the at least one conducting layer has a continuous phase after sintering composed of the material which has a substantial ion conductivity and so that the at least one conducting layer has an ion conductivity effective to conduct ions. A method of producing a gas sensor for detecting small quantities of at least one gas in gas mixtures includes providing a substrate layer composed of ceramic particles composed of a material having substantially no ion conductivity; applying a layer composed of coated ceramic particles onto the substrate layer, the coated ceramic particles being composed of ceramic particles composed of a material that has no substantial ion conductivity coated with a material which has a substantial ion conductivity at the operating temperature of the gas sensor; applying at least one functional layer onto the layer composed of coated ceramic particles to provide a green body; preheating the green body to remove binding agents, plastifying agents, and any additional organic constituents; and sintering the green body after preheating by heating to a temperature effective to sinter the green body so that the layer comprised of coated ceramic particles has a continuous phase comprised of the material which has a substantial ion conductivity.

16 Claims, 1 Drawing Sheet

CERAMIC LAYER SYSTEMS, PARTICULARLY FOR GAS SENSORS

BACKGROUND OF THE INVENTION

The invention relates to ceramic layer systems having at least two adjacent layers whose conductivities are markedly different. Within the scope of this invention, conductivity is to be understood as the property of a material that permits conduction processes under certain conditions. An example of this type of ceramic layer system is included in a specific embodiment of gas sensors, which will be described in detail below, for detecting gases present in small quantities in a surplus of other gases, for example oxygen, carbon monoxide, hydrogen and/or other combustible components in exhaust gases of internal combustion engines. In this case, the conductivities are related to oxygen ion conduction at higher temperatures. The gas sensors being used more frequently in the field are those whose essential elements include a first electrode that is exposed to the gas mixture, a second electrode that is also in contact with the gas mixture by way of a diffusion barrier, and a reference electrode. All of the electrodes are in contact with a material that is ion-conductive at higher temperatures, and are connected to each other in a conductive manner. Zircon dioxide has performed particularly well as an ion-conductive material. Built-in heating elements assure the temperatures at which ion conduction takes place, typically 450 to 800° C. These temperatures are referred to hereinafter as the operating temperature of the gas sensor. The measured signals received by the electrodes indicate the concentrations of the gases to be detected, or changes thereto, and permit control of the operating state of the engine.

The cited components of the gas sensors are mechanically sensitive, and are therefore disposed on a comparatively thick ceramic substrate layer, or embedded into such a substrate layer. The ceramic substrate layer can also be made of zircon dioxide. The advantage of this is that the ceramic substrate layer, which is generally produced from a ceramic substrate film, and the ion-conducting layer, which is generally printed onto the substrate, can be fixedly connected to one another during co-sintering, a stage of the production process, without a phase shift. In the event of temperature changes, therefore, no voltages occur that can have a negative impact on the integrity of the gas sensor. A disadvantage, however, is that the heating elements must be insulated against the ion-conductive ceramic substrate, which can require up to four additional work cycles. A further disadvantage lies in the relatively high cost of zircon dioxide, so the mechanical stability of the sensor is disproportionately high.

The two above-listed disadvantages are avoided if the ceramic substrate comprises a less expensive material that is non-ion-conductive (or practically non-ion-conductive) and therefore does not need to be insulated against the heating elements. Gas sensors of this type contain a ceramic layer system having two adjacent layers of different composition and whose conductivities for oxygen ions vary considerably. The substrate layer is non-ion-conductive (or practically non-ion-conductive), whereas the ion conductivity of the adjacent zircon dioxide layer is higher by several orders of magnitude at the operating temperatures. However, gas sensors that include the materials under practical consideration for the substrate layer have demonstrated that they cannot be sufficiently thermally stressed. In particular, it has been found that first microcracks, then visible, larger cracks form particularly during heating to operating temperatures which, of course, must take place quickly; these cracks soon lead to breakdowns of the gas sensor.

SUMMARY OF THE INVENTION

The ceramic layer systems of the invention are particularly used in gas sensors. Their ceramic substrate layer comprises inexpensive materials, such as aluminum oxide, and the material costs are therefore lower than those of gas sensors whose substrate layer comprises zircon dioxide. Because these inexpensive materials are also non-ion-conducting (or practically non-ion-conducting) at the operating temperatures, the costly insulation of the heating elements can be omitted. The sensors according to the invention can be constructed with a single ceramic substrate film, onto which the functional layers are advantageously applied by means of screen printing. Production costs are also reduced because the printing technique is less expensive than the film technique. The above-described advantages outweigh the additional method step of producing the ceramic particles contained in the ion-conducting layer, which are coated with an ion-conducting material, such as zircon dioxide, The gas sensors having ceramic layer systems in accordance with the invention are on par with those having ceramic substrate layers of zircon dioxide in terms of measuring sensitivity, service life and reliability. Regarding long-term stability, gas sensors having ceramic layers systems according to the invention are clearly superior to the gas sensors of the prior art, which have a substrate layer comprising, for example, aluminum oxide and an adjacent transport layer containing "undiluted" zircon dioxide. Surprisingly, the introduction of ceramic particles of a non-ion-conducting material as a carrier substance for the zircon dioxide in the ion-conducting layer has no noticeable effect on the useful properties of the gas sensor which are associated with the specific conductivity of the ion-conducting layer.

DESCRIPTION OF THE PREFERRED EMBODIMENTS

Figure 1:
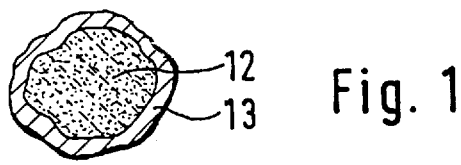
FIG. 1 illustrates a ceramic particle (12) for a ceramic layer system in a gas sensor, the particle being coated with an ion-conducting material (13).
Figure 2:
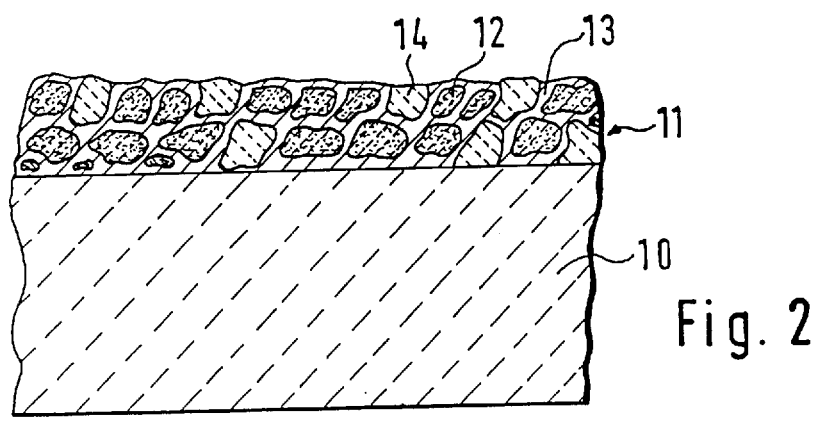
FIG. 2 shows a layer system for a gas sensor comprising a substrate (10) and a conducting layer (11) that contains particles (12) coated with ion-conductive material (13), and uncoated ceramic particles (14).

The ceramic layer systems according to the invention are produced by heating of the so-called green bodies, in which process the ceramic particles of each layer of the green body are sintered to form a mechanically stable, compressed layer and, at the same time, adjacent layers are sintered together and thereby fixedly connected. The ceramic layer systems of the invention are advantageously used for gas sensors for detecting small quantities of gases in gas mixtures, which sensors are produced in accordance with the features of the method claims. They can be exhaust gas sensors, for example, or moisture sensors or sensors for detecting carbon monoxide or carbon dioxide in ventilation air. Depending on the measuring principle, the conductivity then relates to the ionic or electronic conductivity of the relevant materials. Ceramic layer systems according to the invention can also be used in, among other things, electrodes for fuel cells. Then the conductivity relates to the electron conductivity.

Gas sensors having the ceramic layer system of the invention avoid the above-described drawbacks of the prior-art gas sensors mentioned above, and have the advantages described above. With respect to the type and arrangement of the electrodes, the diffusion barriers, and the reception and evaluation of measured signals, the gas sensors of the invention are not notably different from the numerous embodiments known from the prior art. The same also holds true for the heating elements, aside from the fact that they need not be insulated, as mentioned above. A significant feature of the gas sensors having the ceramic layer systems of the invention is that the conducting layer (11), in this case a layer that conducts oxygen ions, and the ceramic substrate layer (10) comprise different materials whose ion conductivities differ considerably at the operating temperature of the gas sensors. Typically, the difference is at least four powers of ten, so the heating elements need not be insulated against the ion-conductive layer.

The ceramic substrate layer (10) comprises an inorganic material that is typically oxidic, exhibits no conductivity or practically no conductivity for oxygen ions, and is stable up to a maximum working temperature of approximately 800° C. Examples of these materials are aluminum oxide and magnesium oxide. Oxide mixtures and compounds of different oxides are also suitable, such as the magnesium silicate $Mg_2SiO_4$, known as forsterite, and particularly the aluminum silicate known as mullite and having changing $Al_2O_3:SiO_2$ ratios, such as $3Al_2O_3.2SiO_2$ to $2Al_2O_3.SiO_3$, with a disordered sillimanite structure. The ceramic substrate layers (10) advantageously comprise mullite and, particularly advantageously, aluminum oxide. Powders whose average grain sizes are approximately 0.01 to 2 $\mu$m, particularly approximately 0.2 to 0.8 $\mu$m, are advisably used for producing the green bodies.

An essential feature of the ceramic layer systems according to the invention that are used in gas sensors is that the conducting layer (11) having a considerable conductivity (that is, considerable conductivity for oxygen ions at the operating temperature) contains ceramic particles (12) which themselves have a low conductivity (that is, they exhibit no or practically no oxygen conductivity at the operating temperature), but are coated with a material (13) that has a high conductivity (i.e., a high oxygen ion conductivity at the operating temperature). The conducting layer (11) accordingly exhibits an ion conductivity at the operating temperature that is considerably higher than that of the ceramic substrate layer (10), but is considerably high in comparison to that of the material (13) and, in any event, is sufficiently high for use in gas sensors. The ion conductivity of the conducting layer is generally at $3.10^{-4}$ to $8.10^{-4}$ $(\Omega cm)^{-1}$, while the ion conductivity of the zircon dioxide, for example, is at $10^{-3}$ $(\Omega.cm)^{-1}$ at the same temperature.

Tetragonal or cubic zircon dioxide is preferred as the highly ion-conductive material in the conducting layer (11). Another suitable ion-conductive material is, for example, bismuth(III) oxide. The zircon dioxide must contain a sufficient proportion, usually 3.5 to 5 molecular percent, of one of the known stabilizers, such as yttrium(III) oxide, scandium(III) oxide, magnesium oxide or calcium oxide, which stabilizes the ion-conductive modification of the zircon dioxides.

The ceramic particles (12) can be selected from the same materials listed above for the ceramic substrate layer (10).

They are preferably made of mullite. The ceramic particles (12) must be fine-particled so that an impenetrable, cohesive phase is formed during sintering.

As in the materials for the ceramic substrate layer, the average grain size should be approximately 0.01 to 2 $\mu$m, preferably approximately 0.2 to 0.8 $\mu$m.

The materials for the ceramic substrate layer (10) and the ceramic particles (12) are advisably selected such that, with the quantity ratios of the components of the conducting layer (11) discussed below, the thermal expansion coefficient of the conducting layer (11) more closely approaches the thermal expansion coefficient of the ceramic substrate layer (10) than does the thermal coefficient of the ion-conducting material (13). The more closely the thermal expansion coefficient of the ion-conducting layer (11) approaches that of the ceramic substrate layer (10), the better the long-term stability of the gas sensors. The above-mentioned selection of the materials is based on the recognition that the thermoshock and the breakdown that it triggers in the gas sensors of the prior art can be attributed to tensions at the phase boundary surface between the ion-conducting layer (11) and the ceramic substrate layer (10); these tensions occur particularly during heating of the sensors to the operating temperature, which causes the clearly different thermal expansion coefficients of the relevant materials.

The ceramic particles (12) are coated with the ion-conducting material (13) in a conventional manner. This can be effected by means of, for example, sputtering of the corresponding metal, such as zircon, onto the swirled or stirred, fine-particle carrier substance in an oxidizing atmosphere. Stabilized zircon is sputtered in that zircon is used as a cathode that contains appropriate quantities of the alloyed metals that yield the above-mentioned stabilizing oxides. The fine-particle carrier substance can also be coated in a sol gel method. In this instance, the fine-particle carrier substance, and possibly one or more further metal alkoxides that yield the above-mentioned oxides, can be suspended in an alcoholic solution of a corresponding metal alkoxide, such as zircon tetraethylate, and the hydroxides precipitate onto the fine-particle carrier substance when water or diluted ammonia is added slowly. When the separated, coated carrier substance is heated to approximately 200 to 400° C., these hydroxides yield the desired oxide layer.

It is crucial for the useful properties of the gas sensor that the ratio of the grain size of the ceramic particles (12) to the layer thickness of the ion-conducting material (13) be selected optimally. In this regard, a conflict of objectives often occurs in that, on the one hand, in the interest of providing sufficient conductivity of the ion-conducting layer (11), a relatively large proportion of ion-conducting material (13), and therefore the greatest possible layer thickness, is desired. The proportion of ion-conducting material (13) should be at least large enough that a continuous phase of ion-conducting material (13) results that covers the ceramic particles (12), although ion-conducting material (13) seeps out of the grain boundaries and into the hollow spaces between the ceramic particles (13). On the other hand, the desire for the greatest possible similarity between the thermal expansion coefficient of the ion-conducting layer (11) and that of the ceramic substrate layer requires the smallest possible proportion of ion-conducting material (13) and thus small layer thicknesses. This is the case, for example, when zircon dioxide is the ion-conducting material, and both the ceramic substrate layer (10) and the ceramic particles (12) are made of mullite. Here the solution to the conflict of objectives lies in the smallest possible quantities of zircon dioxide. The optimum quantity ratio of zircon dioxide (13)

to ceramic particles (12) for an assumed average grain size of the ceramic particles (12) can be readily determined with orienting experiments. However, even with non-optimum quantity ratios, the useful properties of the corresponding gas sensors, and particularly long-term stability, are clearly better than those of gas sensors containing "undiluted" zircon dioxide as an ion-conducting layer (11) and a ceramic substrate layer of mullite.

The following theoretical considerations are also helpful in the purposeful selection of the thickness of the layer comprising ion-conducting material (13). According to Coble, Sintering Crystalline Solids, I. Intermediate and Final State Diffusion Models, J. Appl. Phys. 32 (1961), page 787 et seq., it can be assumed that the structure grain in the phase sintered to be impervious is virtually identical to the tetrakaidecahedron shape of the body that fills space in an ideal manner according to Kelvin. Its inner spherical diameter is 0.88 times the diameter of a sphere of identical volume. If it is assumed that the layer thickness x corresponds to the difference in the radii of the sphere of identical volume and the inner sphere, the following relationship results for the ratio of the layer thickness x to the radius R of the ceramic particles (12) (assumed to be spherical):

$$\frac{x}{R} \geq \frac{0.12}{0.88} 0.14$$

The volume proportion $v_{ion}$ of the ion-conducting material (13), whose volume is characterized as $v_{ion}$, is then $$v_{ion} = \frac{V_{ion}}{V_{tot}} = 1 - \frac{1}{1 + x/R}$$

with respect to the total volume $V_{tot}$ comprising the volumes of the ion-conducting material (13) and the ceramic particles (12).

For x/R=0.14, the resulting volume proportion $v_{ion}$ of the ion-conducting material (13) is 0.33, corresponding to 33 percent.

In accordance with the mixing principle, the thermal expansion coefficient $\alpha_{tot}$ of the ion-conducting layer (11) can be estimated fairly accurately from the thermal coefficient of the ceramic particles part and the thermal expansion coefficient $\alpha_{ion}$ of the ion-conducting material (13):

$$\alpha_{tot} = \alpha_{part} + (\alpha_{ion} + \alpha_{part}) v_{ion}$$

Figure 3:
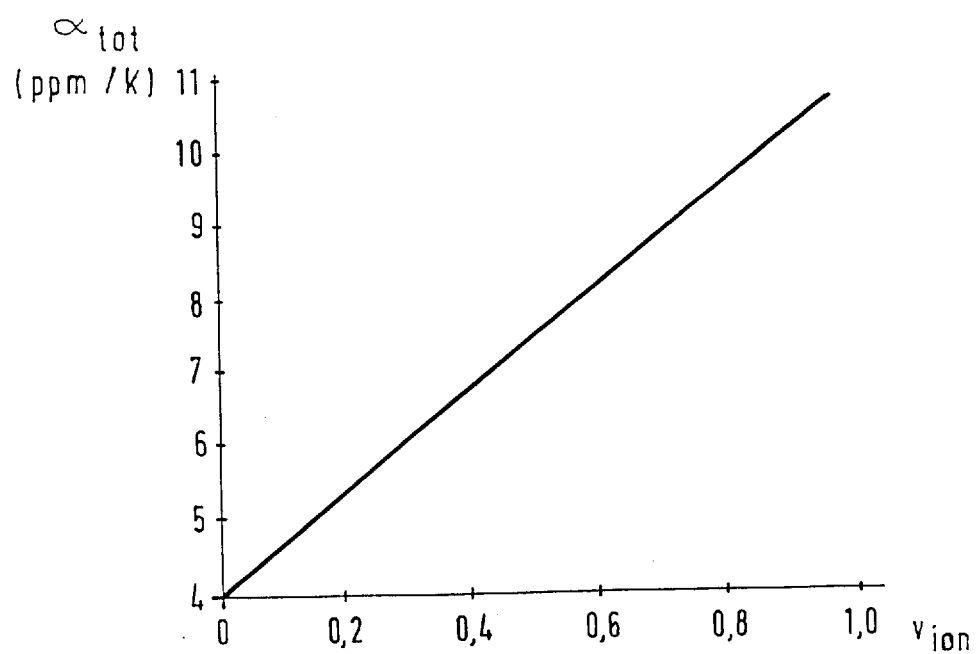
FIG. 3 illustrates the connection between the percent by volume $v_{ion}$ of the ion-conducting material in an ion-conducting layer comprising mullite particles coated with zircon dioxide as an ion-conducting material, and the thermal expansion coefficient of this conducting layer.

In the case that the ceramic carrier comprises aluminum oxide ($\alpha Al_2O_3$=7.7 ppm/K), the ceramic particles (12) in the ion-conducting layer (11) comprise mullite ($\alpha_{mull}$=4 ppm/K) and zircon dioxide ($\alpha ZrO_2$=11 ppm/K) is the ion-conducting material (13), a volume proportion $v_{ion}$ of 0.4 to 0.5 of the zircon dioxide, which corresponds to 40 to 50 percent by volume, is necessary for the thermal percent by volume, is necessary for the thermal expansion coefficient of the ion-conducting layer (11) to match that of the ceramic substrate layer (10). This can be seen in FIG. 3, which illustrates the linear connection between the volume proportion $v_{ion}$ of the zircon dioxide to the mullite particles (12) coated with zircon dioxide (13) and the thermal expansion coefficient $\alpha_{tot}$ of the ion-conducting layer (11). Accordingly, the following relationship would have to apply to the layer thickness to be set:

$$0.2 \leq \frac{x}{R} \leq 0.3$$

In the use of ceramic particles (12) coated with the ion-conductive material (13), it is often advisable to additionally use uncoated particles (14) of the same or a different ceramic material. This is a further option of making the thermal expansion coefficient of the conductive layer (11) similar to that of the ceramic substrate layer (10) with purposeful selection of material. However, it must be noted that the ion-conductive material (13) must be present in the conducting layer (11) in a sufficient quantity to form a continuous phase and thus assure a sufficient ion conductivity, as described above.

In constructing the sensors of the invention, it is advisable to begin with a substrate film produced in a conventional manner from a material that exhibits practically no ion conductivity at the operating temperatures of the gas sensor. Functional layers are applied to this substrate film in a conventional manner, for example in screen printing. First, an ion-conductive layer is printed on one side of the substrate film, and the further functional layers are subsequently printed onto it. The heating elements, which are electrically insulated against the ion-conducting layer, are printed onto the other side of the substrate film. A thick-layer paste produced from the carrier substance coated with the ion-conductive material is used to print the ion-conducting layer. Like the substrate film, it contains the usual binding and plastifying agents and possibly further typical additives, such as solvents for establishing a consistency suitable for printing.

Once the last functional layer has been printed, the green body, that is, the entire layer system, is first freed from the binding and plastifying agents and other possible organic components in a known manner by means of heating, and then sintered at higher temperatures, again in a known manner.

What is claimed is:

1. A ceramic layer system including at least two layers having respective ion conductivities which are substantially different, the ceramic layer system comprising:
   a substrate layer which is comprised of a ceramic material and which has substantially no ion conductivity; and
   at least one conducting layer which is positioned adjacent to the substrate layer, which contains coated ceramic particles comprised of ceramic particles comprising a ceramic material and having no substantial ion conductivity which are coated with a material which has a substantial ion conductivity so that each conducting layer of the at least one conducting layer has a continuous phase after sintering comprised of the material which has a substantial ion conductivity and so that the at least one conducting layer has an ion conductivity effective to conduct ions.

2. The ceramic layer system according to claim 1, wherein the ceramic material of the substrate layer is comprised of ceramic particles, and wherein the ceramic layer system is produced by layering the ceramic particles of the substrate layer and the coated ceramic particles of the at least one conducting layer to form a green body and heating the green body so that the ceramic particles of each layer of the green body are sintered to form a mechanically stable, compressed layer and so that adjacent layers are fixedly connected together by sintering.

3. The ceramic layer system to claims 1, wherein the substrate layer and the at least one conducting layer have respective thermal expansion coefficients which are approximately equal.

4. The ceramic layer system according to claims 1, wherein the at least one conducting layer further comprises uncoated ceramic particles which have no coating and which are comprised of a ceramic material which may be the same as or different from that of the ceramic particles of the coated ceramic particles.

5. The ceramic layer system according to claim 4, wherein the uncoated ceramic particles in the at least one conducting layer are present in an amount ranging up to 20 percent by volume.

6. The ceramic layer system according to claims 1, wherein the system is part of a gas sensor for detecting small quantities of at least one gas present in a gas mixture, and wherein the at least one conductive layer is ion conductive of oxygen ions.

7. The ceramic layer system according to claim 6, wherein the material which coats the coated ceramic particles is zircon dioxide which is stabilized.

8. The ceramic layer system according to claim 7, wherein the zircon dioxide is stabilized by a material selected from the group consisting of scandium(III) oxide, yttrium(III) oxide, magnesium oxide, and calcium oxide.

9. The ceramic layer system according to claims 6, wherein the substrate layer comprises at least one material selected from the group consisting of aluminum oxide and mullite.

10. The ceramic layer system according to claims 6, wherein the ceramic particles of the coated ceramic particles comprise mullite.

11. The ceramic layer system according to claim 1, wherein the ceramic layer system consists essentially of the substrate layer and the at least one conducting layer.

12. The ceramic layer system according to claim 1, wherein the ceramic layer system further comprises at least one functional layer provided on the at least one conducting layer.

13. The ceramic layer system according to claim 12, wherein the ceramic layer system consists essentially of the substrate layer, the at least one conducting layer, and the at least one functional layer.

14. A method of producing a gas sensor for detecting small quantities of at least one gas in gas mixtures, comprising:
   providing a substrate layer comprised of ceramic particles comprising a material which has substantially no ion conductivity;
   applying a layer comprised of coated ceramic particles onto the substrate layer, the coated ceramic particles being comprised of ceramic particles comprising a material that has no substantial ion conductivity coated with a material which has a substantial ion conductivity at the operating temperature of the gas sensor;
   applying at least one functional layer onto the layer comprised of coated ceramic particles to provide a green body;
   preheating the green body to remove binding agents, plastifying agents, and any additional organic constituents; and
   sintering the greed body after preheating by heating to a temperature effective to sinter the green body so that the layer comprised of coated ceramic particles has a continuous phase comprised of the material which has a substantial ion conductivity.

15. The method according to claim 14, wherein the ceramic particles of the substrate layer comprises a material selected from the group consisting of aluminum oxide and mullite, wherein the ceramic particles of the layer comprised of coated ceramic particles comprise mullite, and wherein the material that is conductive of ions at the operating temperature of the gas sensor is zircon which is stabilized.

16. The method according to claim 14, wherein the layer comprised of coated ceramic particles further comprises uncoated ceramic particles.

* * * * *